United States Patent
Yamada

(10) Patent No.: US 6,848,853 B2
(45) Date of Patent: Feb. 1, 2005

(54) POSITIONER AND IMAGE DIAGNOSTIC APPARATUS

(75) Inventor: Takeshi Yamada, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/413,729

(22) Filed: Apr. 15, 2003

(65) Prior Publication Data
US 2003/0202839 A1 Oct. 30, 2003

(30) Foreign Application Priority Data
Apr. 16, 2002 (JP) ........................................ 2002-113549

(51) Int. Cl.[7] ................................................. F16D 1/00
(52) U.S. Cl. ............................... 403/4; 403/3; 403/352; 403/369; 403/DIG. 8
(58) Field of Search ............................... 403/3, 4, 352, 403/369, DIG. 8; 378/15, 17, 193, 196, 197

(56) References Cited

U.S. PATENT DOCUMENTS

| | | | | |
|---|---|---|---|---|
| 2,216,208 A | * | 10/1940 | Michon | 403/DIG. 8 |
| 2,217,560 A | * | 10/1940 | Michon | 403/DIG. 8 |
| 3,385,624 A | * | 5/1968 | Baclini | 403/4 |
| 3,644,735 A | * | 2/1972 | Vandervelden | |
| 4,115,695 A | | 9/1978 | Kelman | |
| 4,150,791 A | * | 4/1979 | Reynolds et al. | |
| 5,141,357 A | * | 8/1992 | Sherman et al. | 403/4 |

* cited by examiner

Primary Examiner—Daniel P. Stodola
Assistant Examiner—Victor MacArthur
(74) Attorney, Agent, or Firm—Carl B. Horton, Esq.; Armstrong Teasdale LLP

(57) ABSTRACT

For the purpose of stably securing an apparatus to be installed by a simple process, a positioner for securing to a floor an apparatus having positioning holes for receiving therethrough anchor bolts implanted upright in the floor, the positioning holes having a diameter substantially larger than that of the anchor bolts, comprises: a first cylindrical bushing member 21 having at an eccentric position a through hole 21c of a diameter for rotatably fitting one of the anchor bolts; and a second cylindrical bushing member 20 having at an eccentric position a hole 20c of a diameter for rotatably fitting the first bushing member 21, the second cylindrical bushing member rotatably fitting in one of the positioning holes provided in the apparatus to be positioned.

7 Claims, 11 Drawing Sheets

POSITIONER AND IMAGE DIAGNOSTIC APPARATUS

CROSS REFERENCE TO RELATED APPLICATIONS

This application claims the benefit of Japanese Application No. 2002-113549 filed Apr. 16, 2002.

BACKGROUND OF THE INVENTION

The present invention relates to a positioner for securing an apparatus to a floor, and an image diagnostic apparatus.

Medical apparatuses, particularly X-ray CT and MRI systems, require an apparatus for scanning a subject (called a gantry), and an apparatus for carrying the subject rested thereon to a scanning position. In such medical apparatuses, to which region (position) in the subject a reconstructed tomographic image relates is very important.

Therefore, high positioning accuracy is naturally required when installing a medical apparatus in a health care facility (e.g., a hospital).

Positioning of, for example, a gantry is conducted as follows: First, an installation location for the medical apparatus is decided. At the time of this decision, the positions that positioning holes provided beforehand in a base plate (an iron plate) of the gantry will assume relative to the floor when the gantry position is fixed are ascertained.

After deciding the installation location, anchor bolts (usually of metal) are implanted upright at corresponding positions on the floor, as shown in FIG. 10(*a*). Usually, holes are bored by means of a drill or the like when the floor is of concrete, for example, and anchor bolts having threads are implanted; however, any technique may be used.

Each anchor bolt is then led through the positioning hole in the base plate of the gantry (FIG. 10(*b*)), and the gantry is finally secured by the anchor nut (FIG. 10(*c*)).

An advantage of such a positioning method is that once positioning of the apparatus has been completed, stable securement at that position is possible so long as the diameter of the positioning holes in the base plate of the apparatus to be installed (here the gantry) is tight with respect to the anchor bolts. However, high accuracy is required for the implanting positions of the anchor bolts; and if reinforcing steel is buried under the floor where an anchor bolt is to be implanted and the anchor bolt cannot reach a prescribed depth, the implanting positions for all the remaining anchor bolts must be modified. That is, the initially intended installation position for the apparatus must be changed.

Moreover, it is generally common for a machine supplier to take charge of the drilling work for implanting the anchor bolts and for a maintenance service provider to take charge of positioning of the apparatus. Therefore, if the problem described above emerges, additional time is required for communication and preparation, thereby delaying the start of operation of the apparatus in the hospital or other such health care facility.

To solve such a problem, the diameter of each positioning hole in the base plate of the apparatus to be installed may be made larger than the diameter of the anchor bolt (e.g., ca. 3–5 times larger than the diameter of the anchor bolt), and a washer having a larger diameter than that of the positioning hole may be interposed between the positioning hole in the base plate of the apparatus to be installed and the anchor bolt for securing the apparatus, as shown in FIG. 11.

An advantage of such a method is that high accuracy is not required for the implanting positions for the anchor bolts. Moreover, even if reinforcing steel is buried under the floor at the target position, the anchor bolt may be implanted at another position insofar as the diameter of the positioning hole permits. That is, the method is advantageous in that modification of an implanting position for one anchor bolt does not lead to modification of implanting positions for other anchor bolts. According to the securing method shown in FIG. 11, however, the apparatus sometimes moves in the horizontal direction due to lateral shaking by an earthquake, etc.

SUMMARY OF THE INVENTION

It is therefore an object of the present invention to provides a positioner by which an apparatus, especially one whose installation position requires high accuracy, can be fixedly secured by a relatively simple process and yet with good accuracy, and an image diagnostic apparatus.

To solve such problems, a positioner of the present invention has, for example, the following configuration: Specifically, a positioner for securing an apparatus to a floor, said apparatus having positioning holes for receiving therethrough anchor bolts implanted upright in said floor, said positioning holes having a diameter substantially larger than that of said anchor bolts, comprises:

- a first cylindrical bushing member having at an eccentric position a through hole of a diameter for rotatably fitting one of said anchor bolts; and
- a second cylindrical bushing member having at an eccentric position a hole of a diameter for rotatably fitting said first bushing member, said second cylindrical bushing member rotatably fitting in one of said positioning holes.

According to the present invention, an apparatus to be installed can be stably secured by a simple process. Therefore, the present invention is especially effective for a medical apparatus whose installation position requires high accuracy and which is relatively large and heavy.

Further objects and advantages of the present invention will be apparent from the following description of the preferred embodiments of the invention as illustrated in the accompanying drawings.

DETAILED DESCRIPTION OF THE INVENTION

Embodiments in accordance with the present invention will now be described in detail with reference to the accompanying drawings.

<General Description>

Figure 1:
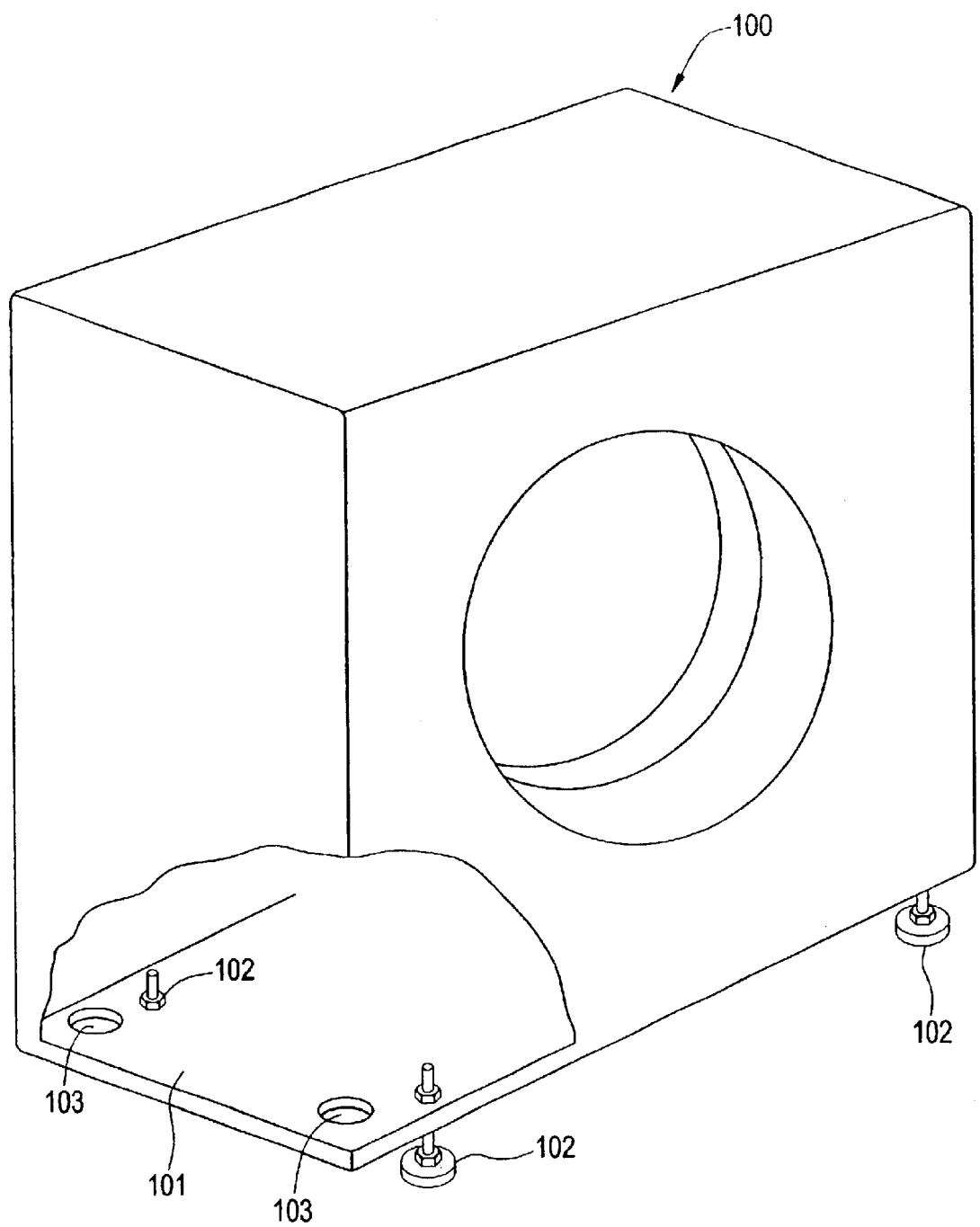
FIG. 1 is a partially broken exterior perspective view of a medical apparatus in accordance with one embodiment.

FIG. 1 shows a partially broken exterior view of a gantry in an X-ray CT system. Although the gantry 100 has therein a rotator supporting an X-ray tube an X-ray detecting section known in the art, they are not directly concerned with the present invention and are omitted.

In FIG. 1, reference numeral 101 designates a base plate (a metal plate such as an iron plate), which is provided near its four corners with adjusters 102 for height adjustment (and also for tilt adjustment) and positioning holes 103. In an embodiment, the diameter of each positioning hole is 5 times larger than that of an anchor bolt (which will be described later) so that the implanting position for the anchor bolt is permissible within an appropriate range. It is assumed hereinbelow that the anchor bolt has a diameter represented by $\phi$ (e.g., 1.5 cm) and the positioning hole has a diameter represented by $R_0$ (=5$\phi$), but the present invention is not limited by the value or factor.

In the present embodiment, there are proposed positioners for securing the gantry 100 using the positioning holes 103.

Figure 2A:
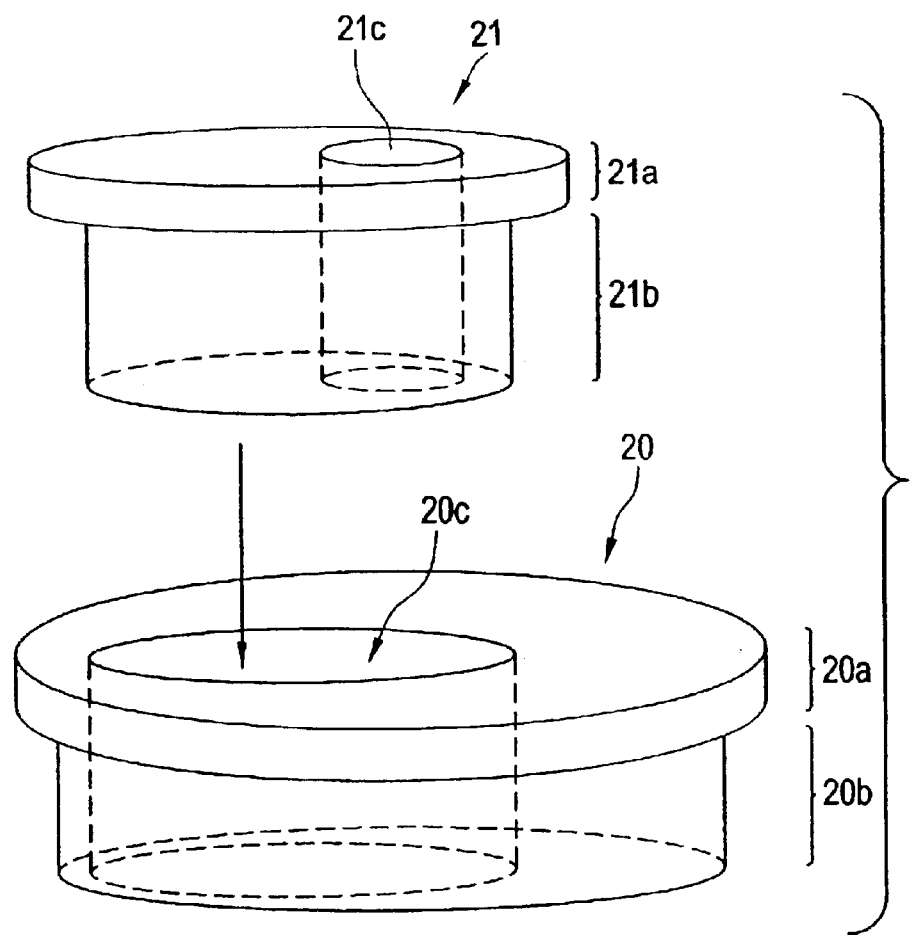
FIG. 2 shows a structure of a positioner in the embodiment.

FIG. 2(a) shows a specific structure of one of the positioners. As shown, the positioner is comprised of two cylindrical bushing members 20 and 21 of metal (e.g., iron). (The broken lines represent hidden lines.)

The larger bushing member 20 has a diameter of $R_0$ at a cylindrical portion in a lower part 20b; that is, the lower part 20b has the same diameter as the positioning hole 103 in the gantry 100. Strictly, the diameter is slightly smaller than $R_0$ because the bushing member 20 must be fitted in the positioning hole 103 and also must be rotatable within the positioning hole 103, which will be described later. Moreover, the bushing member 20 is provided in an upper part 20a with a flange for preventing the bushing member 20 from falling out when it is fitted into the positioning hole in the gantry 100.

Furthermore, the bushing member 20 is provided at a position offset from its center axis with a circular hole 20c for receiving therethrough the other bushing member 21. The hole 20c is provided to pass from the upper surface through the lower surface of the bushing member 20. The diameter of the hole 20b is represented by $R_1$.

With respect to the other bushing member 21, the shape thereof is similar to that of the bushing member 20. Specifically, a cylindrical portion in a lower part 21 has a diameter $R_1$ so that the portion 21b can be fit in the hole 20c in the bushing member 20. Since the bushing member 21 must also be fitted in the hole 20c and must be rotatable within the hole 20c, strictly, the lower part 21b has a diameter slightly smaller than $R_1$.

Again, the bushing member 21 is provided in an upper part 21a with a flange for preventing the bushing member 21 from falling out of the bushing member 20 when it is fitted into the hole 20c. Moreover, the bushing member 21 is provided at a position eccentrically offset from its center axis with a hole 21c (of a diameter of $\phi$) for receiving therethrough an anchor bolt. Strictly, the hole 21 is again slightly larger than $\phi$ (or alternatively the diameter of the anchor bolt is slightly smaller than $\phi$), because the anchor bolt must be rotatable when it is fitted into the hole 21c, similarly to the above.

Figure 2B:
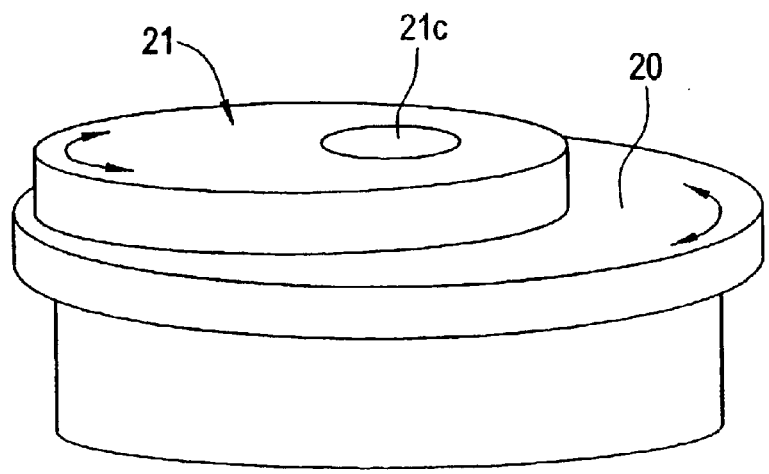

The state in which the bushing member 21 is fitted into the hole 20c of the bushing member 20 in the foregoing configuration is shown in FIG. 2(b); the bushing member 21 is rotatable with respect to the bushing member 20.

Let us consider the range of possible positions of the hole 21c in the bushing member 21 in such a configuration when the bushing member 20 is fitted into the positioning hole 103 in the gantry 100 and the bushing member 21 is fitted into the hole 20c in the bushing member 20.

For simplifying explanation, the flanges 20a and 21a on the bushing members 20 and 21 are ignored, and the outer shape of the lower parts 20b and 21b and the hole 21c are considered for explanation.

Figure 3A:
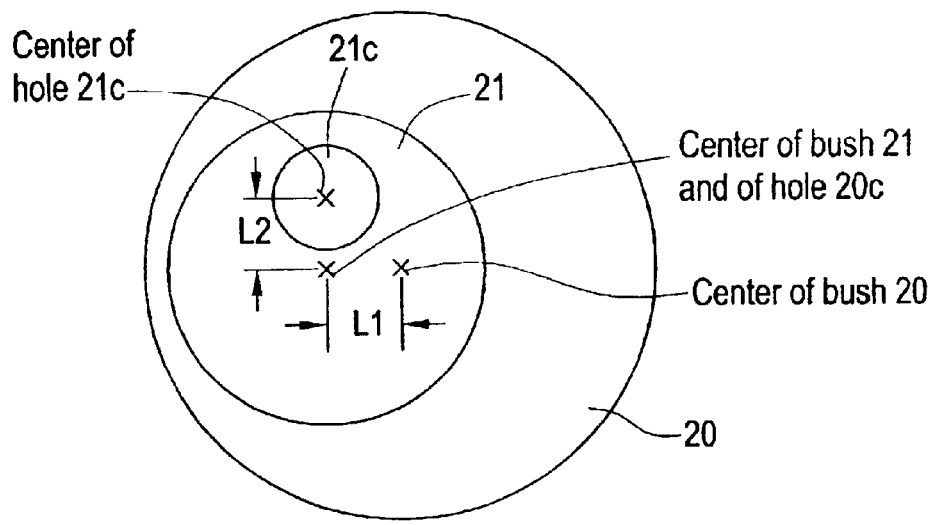
FIG. 3 schematically shows the function of the positioner in the embodiment.
Figure 3B:
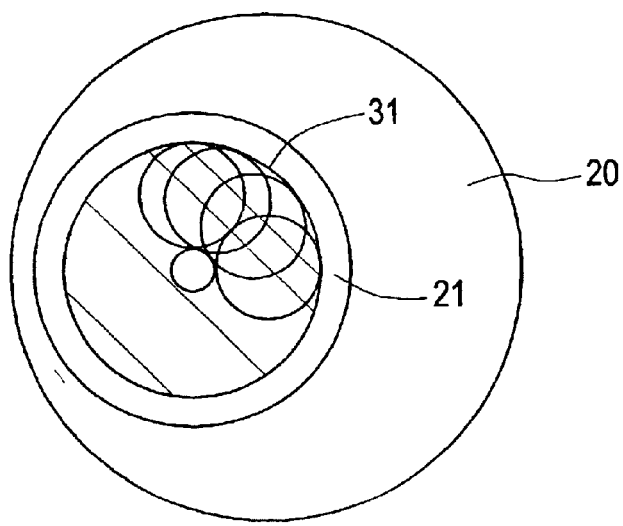

Assume that the bushing members 20 and 21 are in the positional relationship shown in FIG. 3(a). If the bushing member 20 is fixed and the bushing member 21 is rotated, the resulting range of possible positions of the hole 21c in the bushing member 21 is the region designated by reference numeral 31 shown in FIG. 3(b). This means that the position of the hole 21c can be freely changed within the region 31.

Figure 3C:
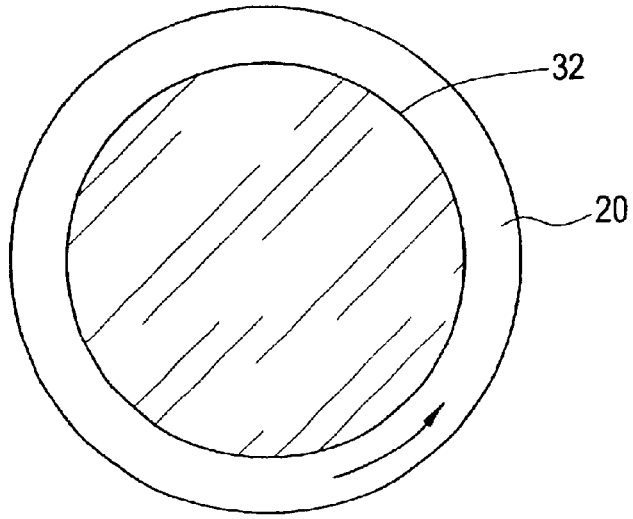

Since the bushing member 20 is rotatably fitted in the positioning hole 103 in the gantry 100, the hole 21c of the bushing member 21 can be freely positioned within a region 32 shown in FIG. 3(c) by rotating the bushing members 20 and 21.

Since the outermost circle shown in FIG. 3(c) corresponds to the circumference of the positioning hole 103 in the gantry 100, the resulting position for implanting the anchor bolt into the floor may be anywhere within the internal region 32 of the positioning hole 103, and the anchor bolt can be secured by the bushing members 20 and 21 within that range, which further means that the gantry 100 can be secured.

Representing the distance from the center of the bushing member 20 to the center of the hole 20c in the bushing member 20 by L1 and the distance from the center of the bushing member 21 to the center of the hole 21c in the bushing member 21 by L2 as shown in FIG. 3(a), it is desirable that $L1 \leq L2$ be satisfied.

Figure 4:
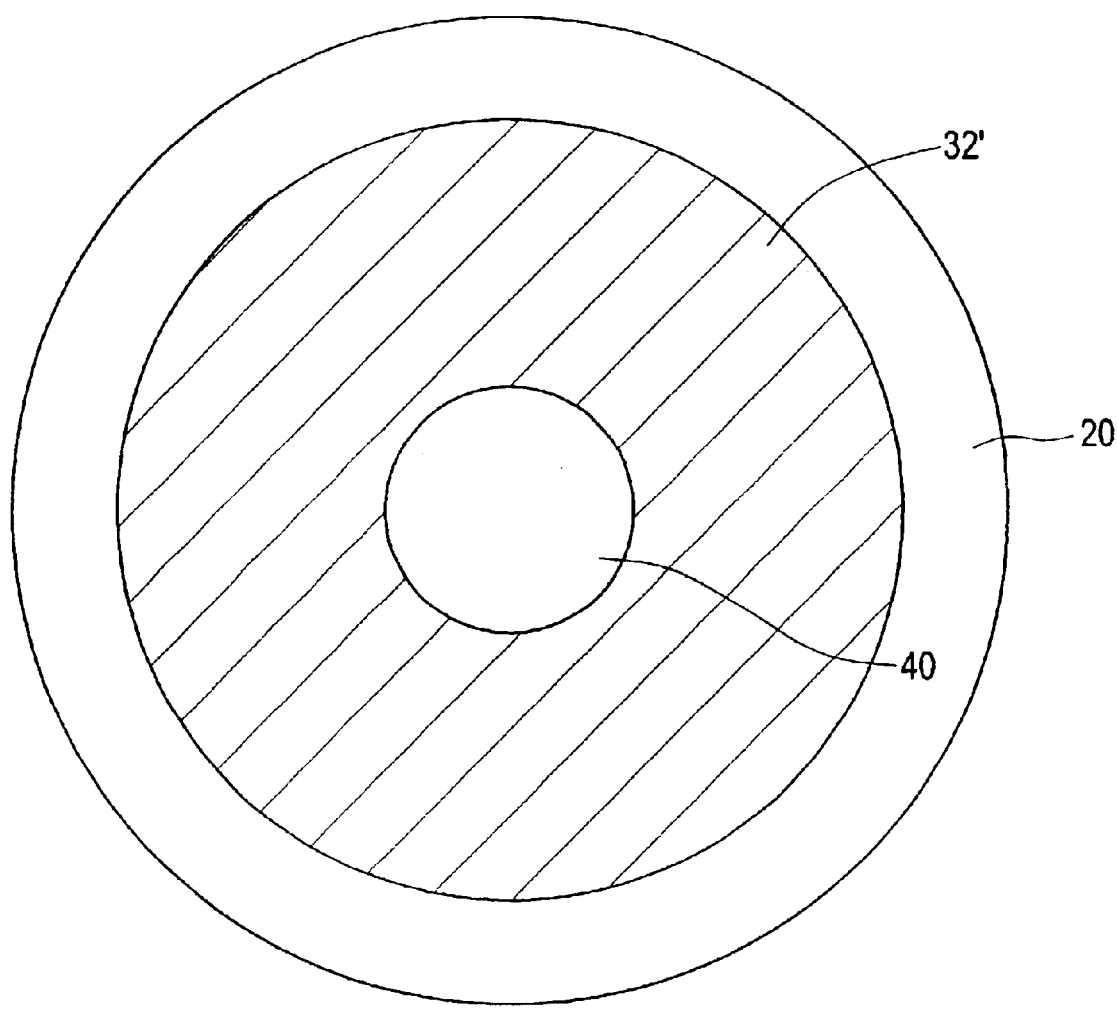
FIG. 4 shows generation of a region in which positioning is impossible by the dimension of bushing members constituting the positioner.

The reason for this is that, if L1>L2, the range of possible positions of the hole 21c becomes the region 32' shown in FIG. 4 and a region 40 near the center position of the bushing member 20 is excluded. More plainly stated, when the position at which the anchor bolt is implanted falls within the center region 40 of the positioning hole 103 in the gantry 100, the anchor bolt cannot be secured by the bushing members 20 and 21. It would be understood that by this reason $L1 \leq L2$ is desirably satisfied as described above.

In light of the preceding description, the procedure of installing a medical apparatus using the positioner of the embodiment consists of the following steps 1–6:

Step 1: A location for installing a medical apparatus (the gantry in this embodiment) is decided.

Step 2: Positions for implanting the anchor bolts are decided based upon the installation location and positions of the positioning holes in the medical apparatus, and the implanting positions are clearly indicated to the service provider who is to implant the anchor bolts. At the same time, the service provider is informed that the anchor bolts may be implanted anywhere within the region 32 shown in FIG. 3(c).

Step 3: The implanting service provider implants each anchor bolt in the specified region. Therefore, if a hole for implanting an anchor bolt is drilled and reinforcing steel or the like happens to obstruct the drilling, the hole for the implantation may be drilled at another position within the specified region to implant the anchor bolt.

Figure 5:
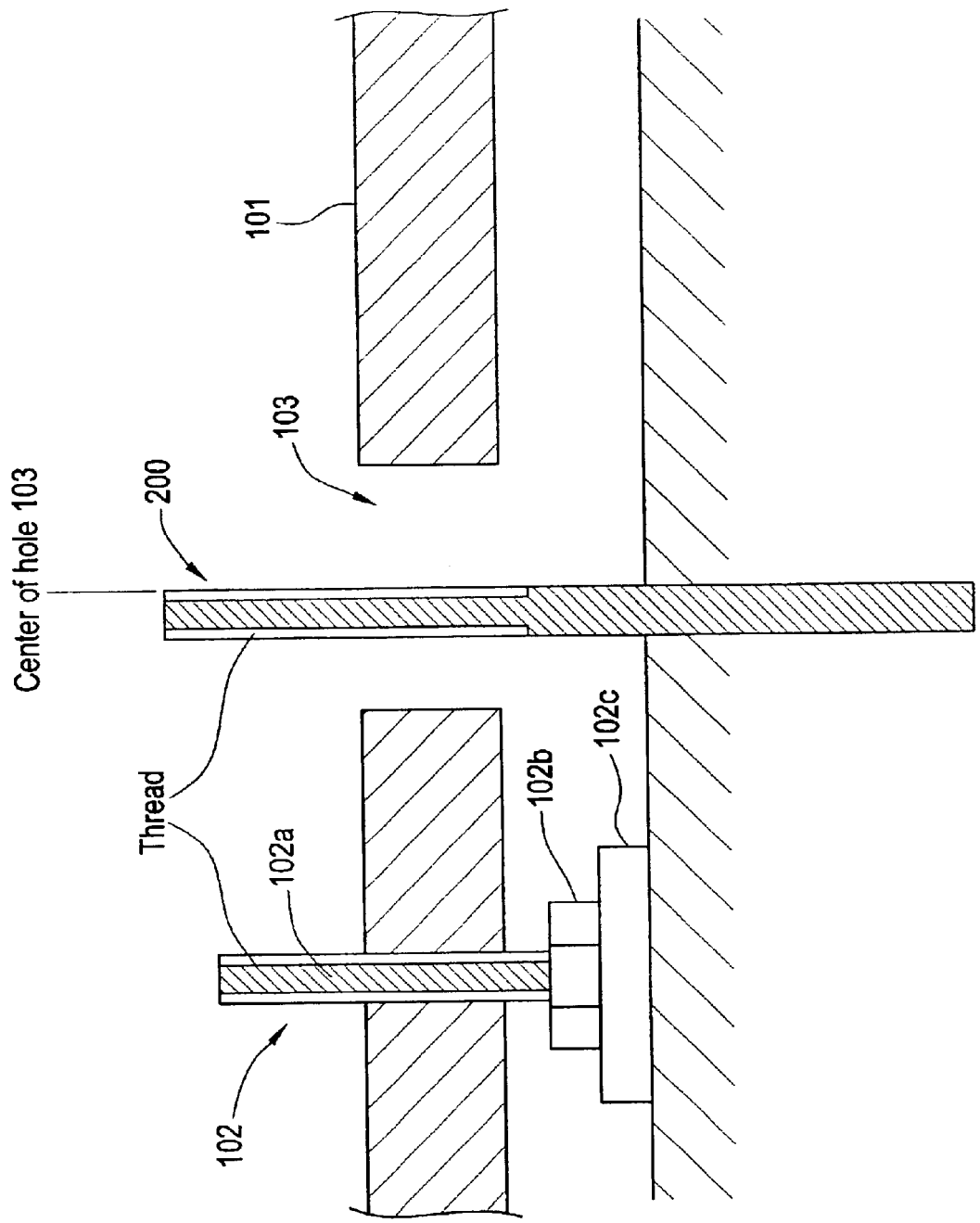
FIG. 5 shows a procedure of positioning in the embodiment.

Step 4: The medical apparatus is installed. At this time, the anchor bolts have been implanted into the floor, and accordingly, the anchor bolts are led through the positioning holes in the medical apparatus. The adjusters 102 are then appropriately set to adjust the medical apparatus so that it is even in height and has no tilt. The condition at this time is shown in FIG. 5. In FIG. 5, the position at which the anchor bolt 200 is implanted is shown as being offset from the center of the positioning hole 103.

The adjuster 102 will be explained here only briefly because it is known in the art. A bolt 102a in the adjuster 102 is threaded so that the thread engages with the base plate 101. A nut 102b unitary with the bolt 102a is rotatable with respect to a base 102c. Thus, when the nut 102b is rotated by a tool or the like, the bolt 102a rotates. Since the base plate 101 is engaged with the bolt 102a, the height of the base plate 101, hence, of the medical apparatus, is consequently adjusted.

Figure 6:
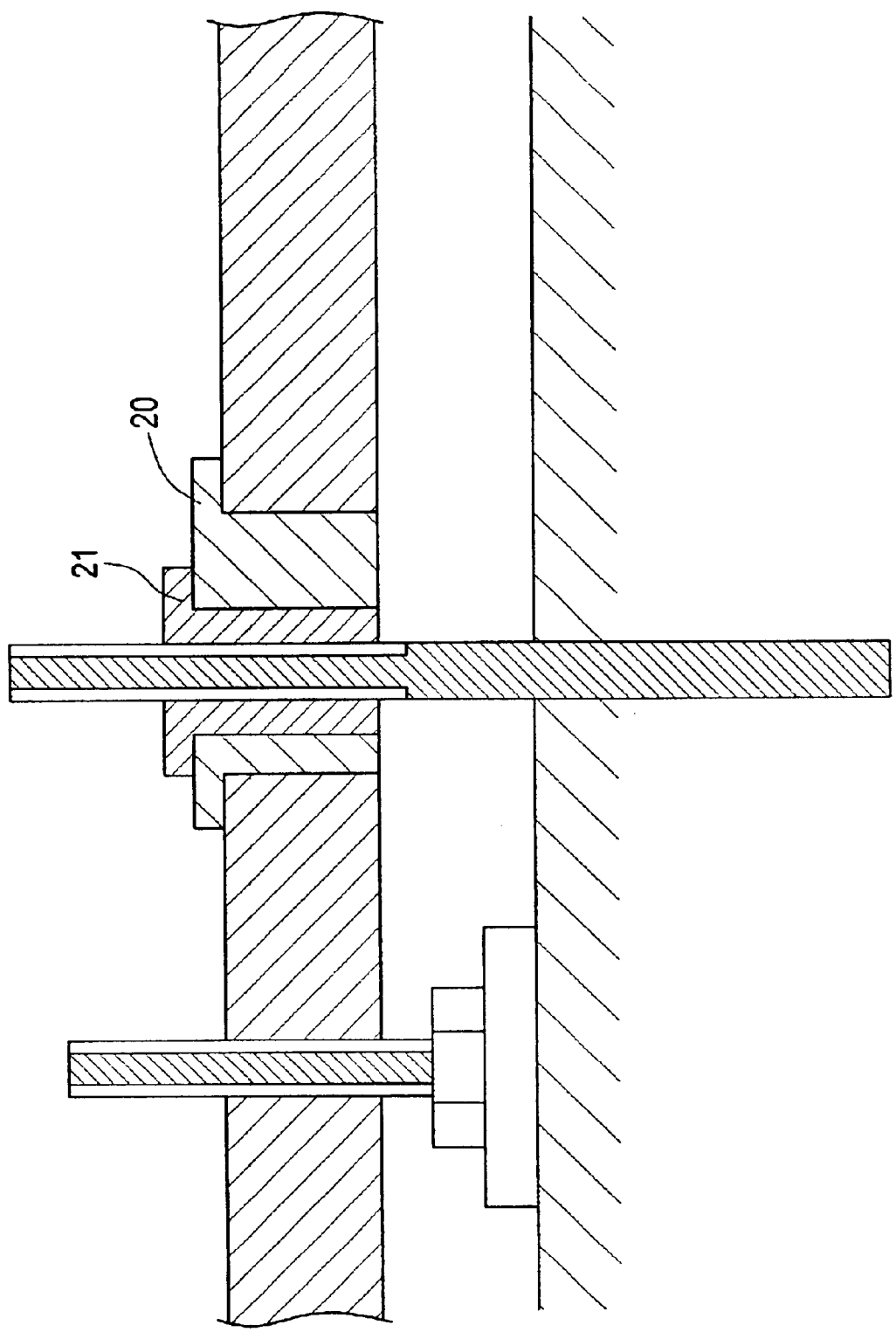
FIG. 6 shows the procedure of positioning in the embodiment.

Step 5: After the height adjustment has been completed, the anchor bolt 200 is passed through the hole 20c in the bushing member 20 (the larger one) and the bushing member 20 is fitted into the positioning hole 103. Thereafter, the anchor bolt 200 is passed through the hole 21c of the bushing member 21 (the smaller one), and the bushing member 21 is fitted into the hole 20 of the bushing member 20 by appropriately rotating the bushing members 20 and 21. This condition is shown in FIG. 6.

Figure 7:
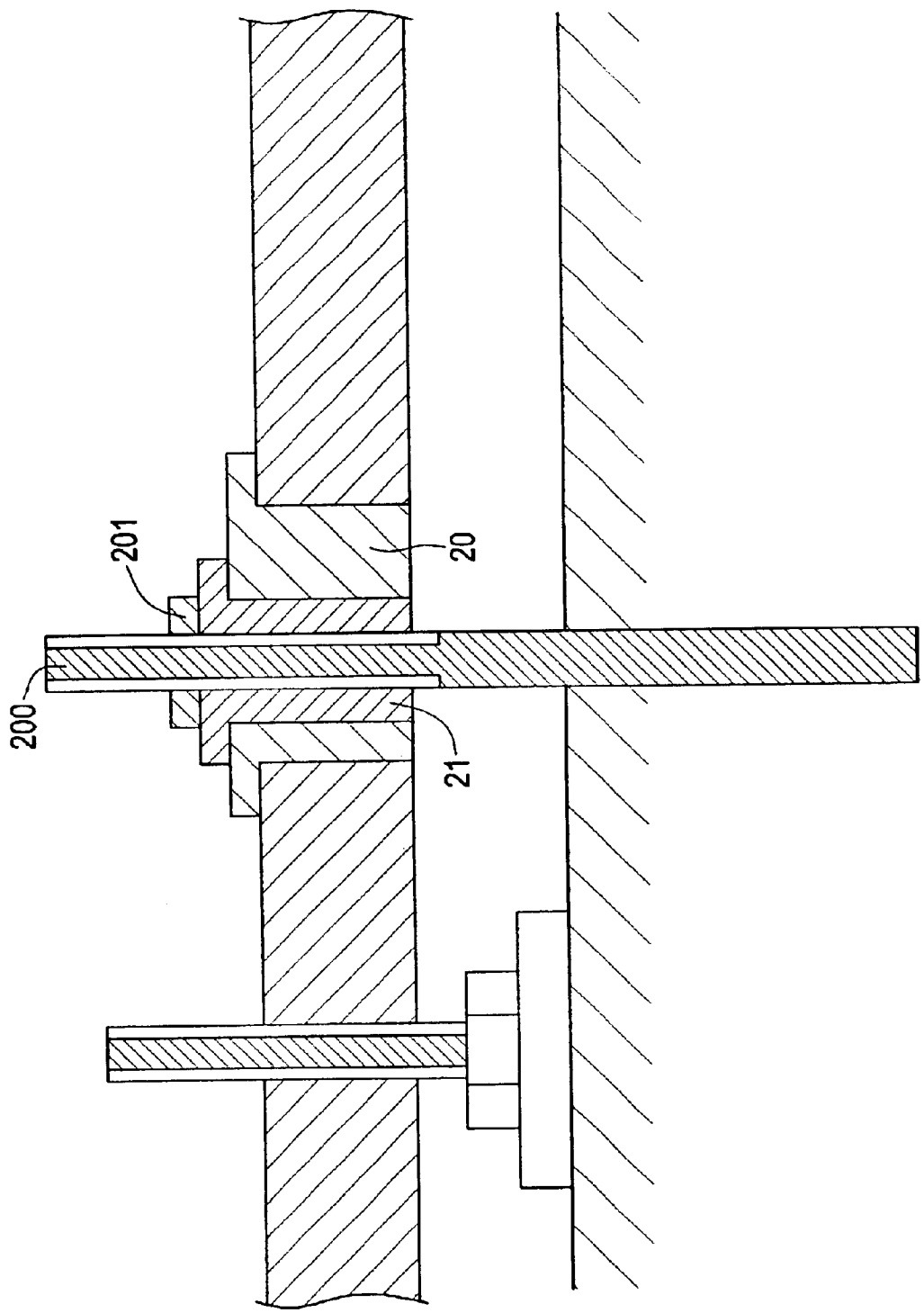
FIG. 7 shows the procedure of positioning in the embodiment.

Step 6: A nut is screwed onto the anchor bolt 200 and is fastened. The result of this is shown in FIG. 7, wherein reference numeral 201 designates the nut.

Step 7: By repeating Steps 4–6 for the other positioning holes 103, positioning of the medical apparatus is completed.

According to the present embodiment as described above, implanting positions for the anchor bolts may be selected within a certain permissible range and do not require high accuracy. Moreover, if an anchor bolt cannot be implanted into an intended position by some reason (e.g., in the case that reinforcing steel happens to be buried at a position for the implantation and a prescribed depth cannot be reached), the anchor bolt may be implanted into another position within the allowed range, and the process need not go back to re-deciding the installation position for the medical apparatus.

Figure 10A:
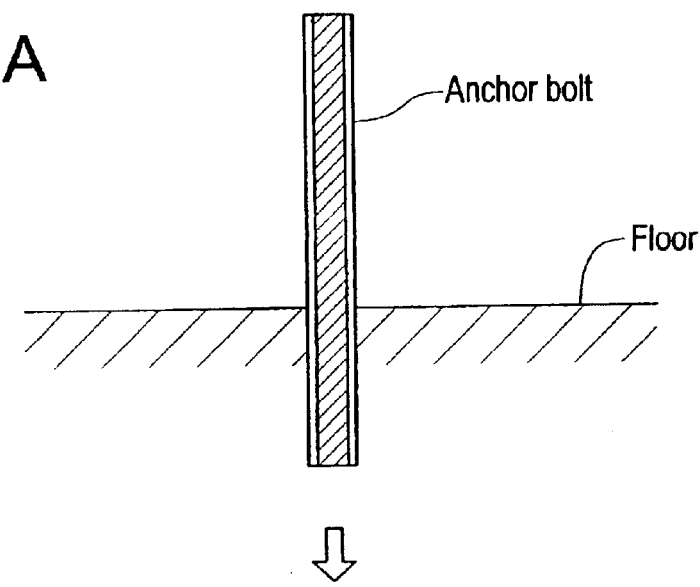
FIG. 10 shows a conventional positioning process.
Figure 10B:
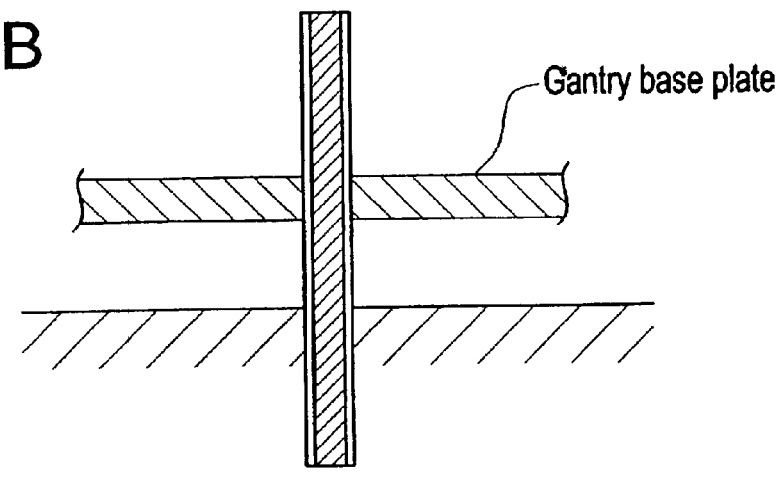
Figure 10C:
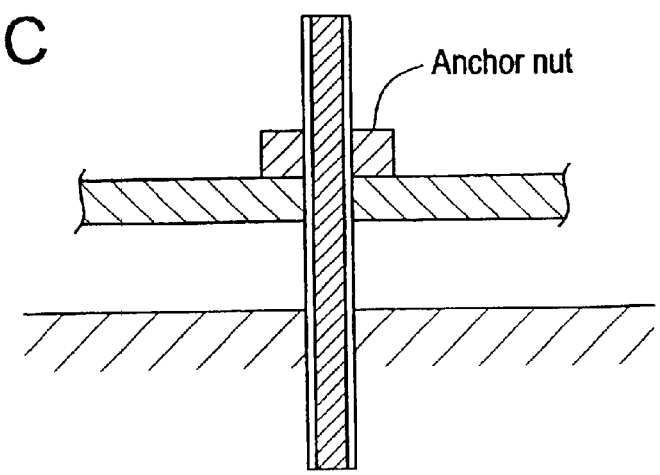
Figure 11:
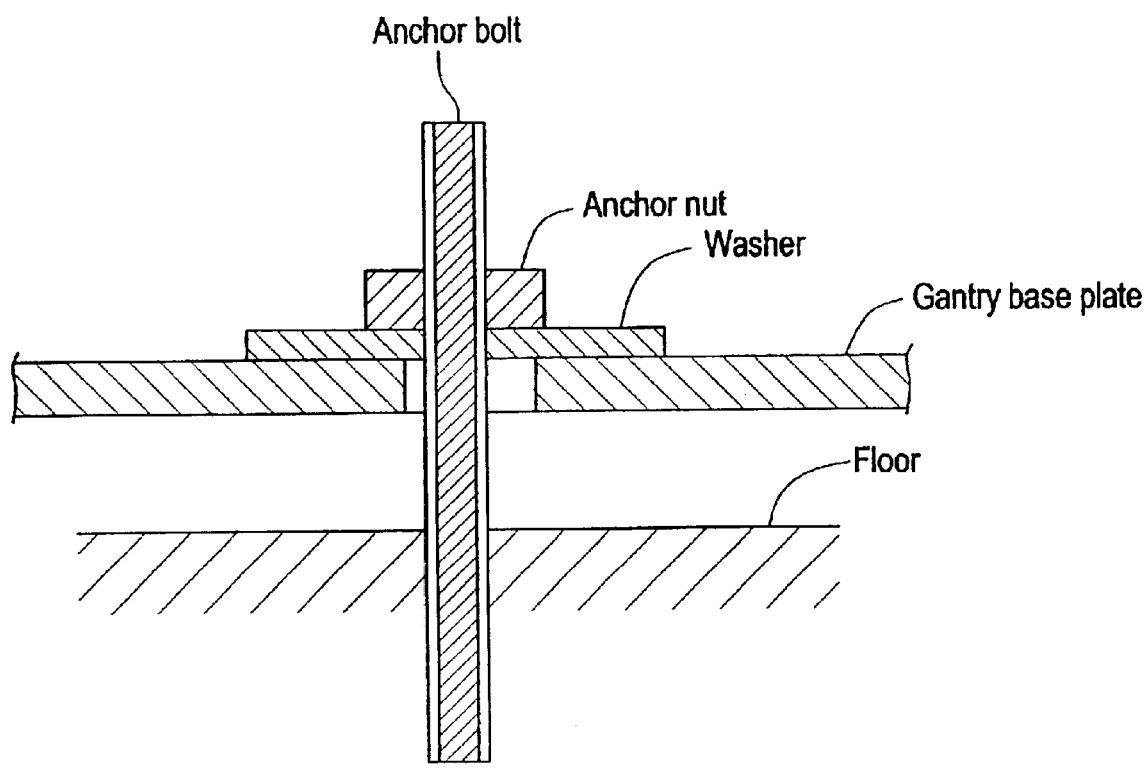
FIG. 11 shows another example of the conventional positioning.

Furthermore, since the diameter of the positioning holes in the medical apparatus may be larger than that of the anchor bolts, the process of installing the medical apparatus is significantly facilitated: The reason for this is that if a positioning hole of the medical apparatus is tight with respect to an anchor bolt and a plurality of such positioning holes are present, the plurality of the anchor bolts must be led through all of the plurality of holes. In addition, once the anchor bolts have been tightly secured by the bushing members 20 and 21, an effect equivalent to that by the anchor bolts 200 tightly secured into the positioning holes in the medical apparatus as shown in FIG. 10 can be achieved, thereby restraining the medical apparatus from movement due to an earthquake etc.

<Second Embodiment>

A configuration in which an adjuster for adjusting the height of a medical apparatus is incorporated into a positioner will now be described as a second embodiment.

Figure 8:
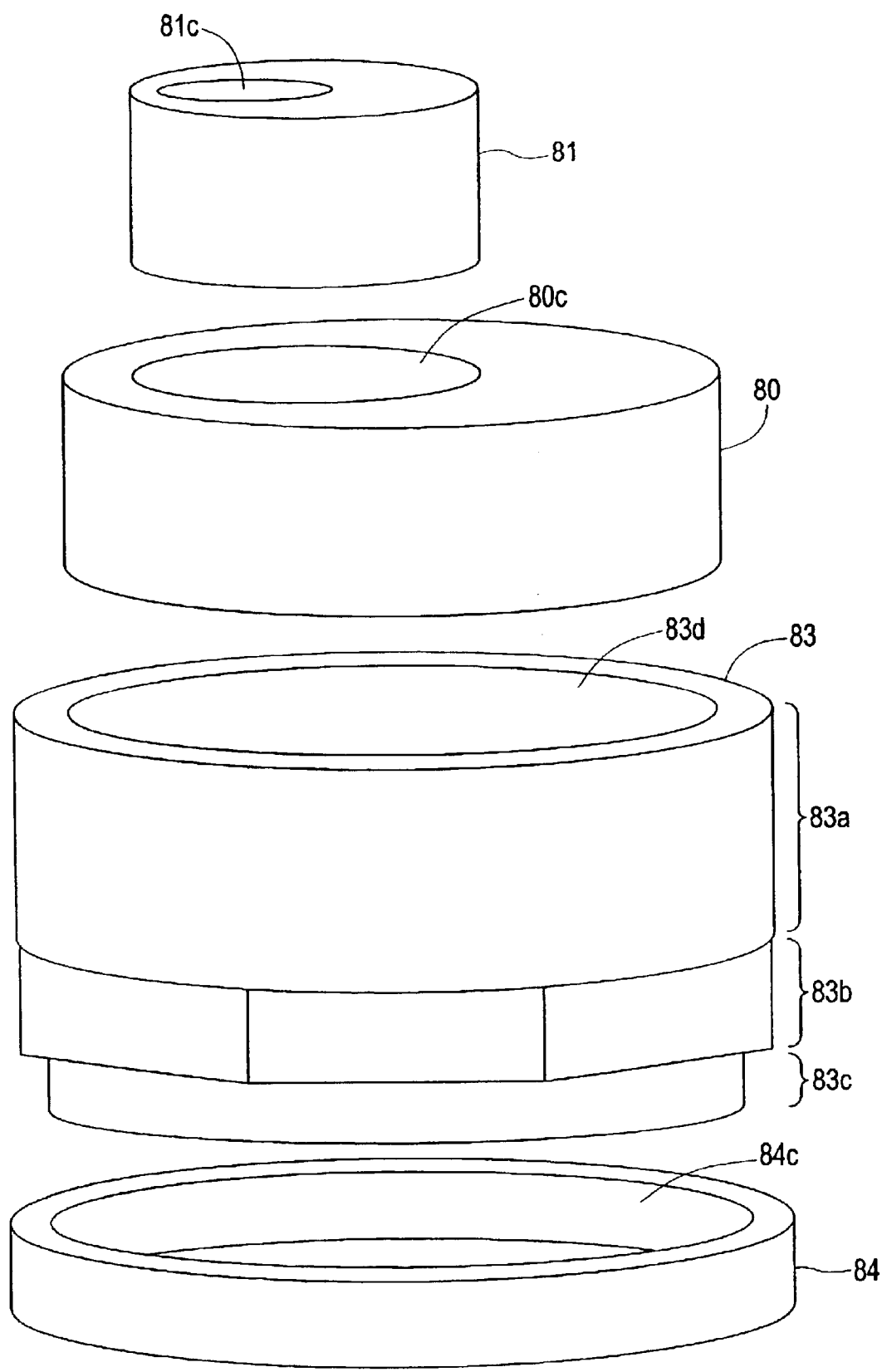
FIG. 8 shows a configuration of the positioner in a second embodiment.

FIG. 8 shows components in such a positioner. In FIG. 8, members designated by reference numerals 80–84 are made of a material having sufficient strength, such as metal (e.g., iron). Members designated by reference numerals 80 and 81 correspond to the bushing members 20 and 21 described in the above embodiment (first embodiment), except that no flanges are provided. It will be easily recognized that holes 80c and 81c correspond to the holes 20c and 21c, respectively.

Reference numeral 83 designates a hollow bolt having a hole 83d with a center position coinciding with the center of the bolt 83, being not eccentric. The diameter of the hole 83 is one such that the bushing member 80 is maintained to be rotatably fitted into the hole 83d (which implies that the diameter is approximately equal to the outer diameter of the bushing member). The bolt 83 is comprised of three members 83a–83c arranged in the height direction, and has a dimension at least higher than the height of the bushing members 80 and 81. The upper part 83a is threaded so that the thread engages with a positioning hole 103 in a medical apparatus (which is again exemplified by the gantry 100 for the sake of simplifying explanation). Reference numeral 83 designates a nut portion (for example, having a hexagonal shape) for rotating the bolt 83. Thus, the bolt 83 is moved with respect to the base plate 101 in the vertical direction by rotating the nut portion 83b. The base part 83c is for fitting it into a hole 84c in an anchor ring 84, so that the bolt 83 is rotatable with respect to the anchor ring 84. The anchor ring 84 serves to facilitate rotation of the bolt 83, that is, to aid the rotation of the bolt 83, and to disperse the weight of the apparatus to be positioned. (Therefore, the outer diameter of the anchor ring 84 is desirably large.)

Since the structure and significance of the bushing members 80 and 81 would be easily recognized with reference to the aforementioned embodiment, the procedure of installing them will be omitted and explanation will be made on a condition after completing securement of the medical apparatus.

Figure 9:
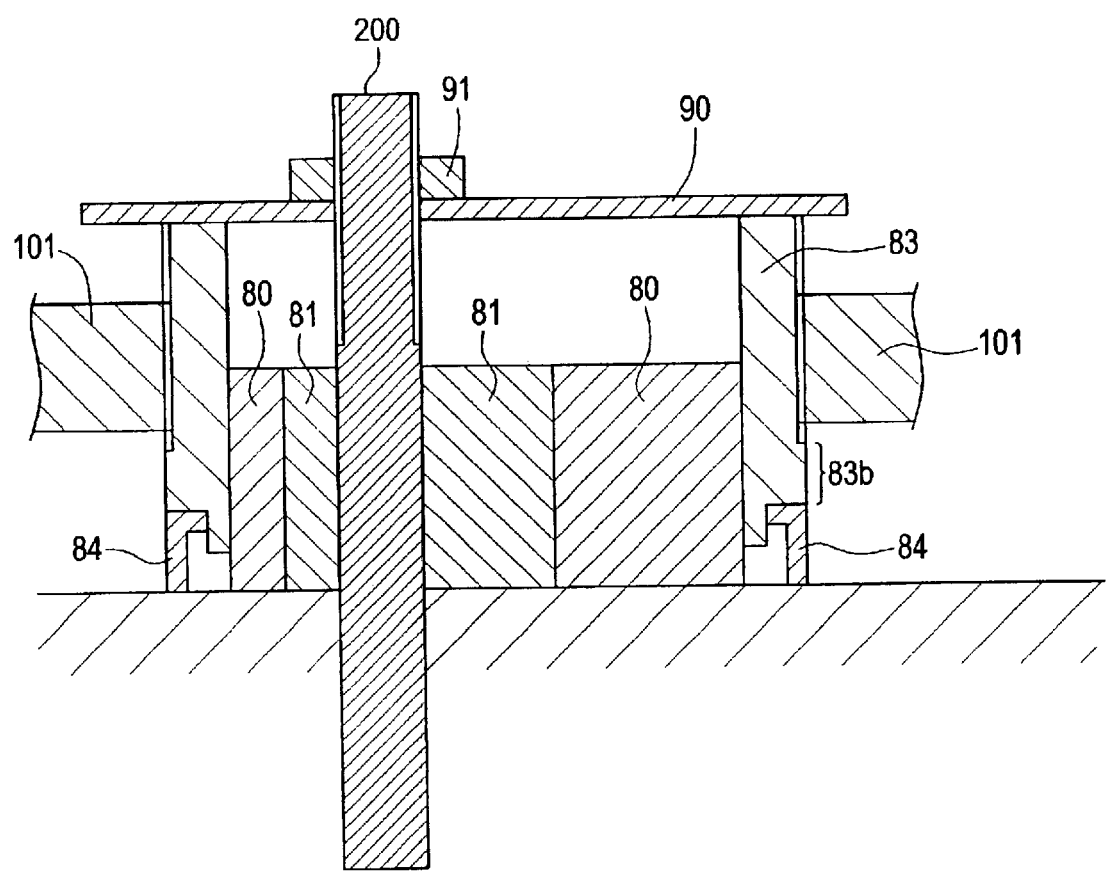
FIG. 9 shows a condition after completing positioning by the positioner in the second embodiment.

FIG. 9 is a cross-sectional view around the anchor bolt 200 after completing positioning of the medical apparatus.

In FIG. 9, newly introduced members in addition to those shown in FIG. 8 are a washer 90 and a nut 91. The diameter of the washer 90 need only be large enough to cover the bolt 83 wherever the anchor bolt is placed within an allowed range.

Referring to FIG. 9 showing the condition after completing the positioning, when the height of the medical apparatus is to be adjusted, it suffices to remove the nut 91 and rotate the nut portion 83b of the bolt 83. This enables the height of the medical apparatus to be adjusted because the bolt 83 engages with the base plate 101 of the medical apparatus 100. After the height has been adjusted, the nut 91 is fastened, which gives a result equivalent to that by combining the nut 91, washer 90 and bolt 83 in one piece, thus fixing the anchor bolt 200 and the height of the medical apparatus.

As a result, according to the second embodiment, the adjuster for setting the height of the apparatus to be installed can be incorporated into the positioner, in addition to achieving the effect of the aforementioned embodiment.

Although description has been made with reference to the CT gantry as the apparatus to be installed (i.e., image diagnostic apparatus) in the first and second embodiments, it will be easily recognized that the apparatus to be installed is not limited thereto. The apparatus to be installed may be substantially any apparatus which is required to be positioned with high accuracy. The present invention is especially effective for a relatively large and heavy apparatus. Such apparatus include MRI, PET, and γ-camera systems, besides the CT system.

Many widely different embodiments of the invention may be configured without departing from the spirit and the scope of the present invention. It should be understood that the present invention is not limited to the specific embodiments described in the specification, except as defined in the appended claims.

What is claimed is:

1. A positioner for securing an apparatus to a floor, said apparatus having positioning holes for receiving therethrough anchor bolts implanted upright in said floor, said positioning holes having a diameter substantially larger than that of said anchor bolts, said positioner comprising:

a first cylindrical bushing member having at an eccentric position a through hole of a diameter for rotatably fitting one of said anchor bolts;

a second cylindrical bushing member having at an eccentric position a hole of a diameter for rotatably fitting said first bushing member, said second cylindrical bushing member rotatably fitting in one of said positioning holes;

a bolt member having thereon a thread for engaging with one positioning hole in said apparatus and a nut portion for enabling rotation, and having a hole for rotatably fitting therein said second bushing member; and a ring member disposed between said bolt member and said floor for aiding rotation of said bolt member, wherein said bolt member includes a base member below said nut portion, said base member configured to fit within a hole of said ring member.

2. The positioner of claim 1, wherein said anchor bolts are implanted into a floor.

3. The positioner of claim 1, wherein a material of which said first and second bushing members and said bolt member are made is metal.

4. The positioner of claim 1, wherein said bolt member has a height larger than those of said first and second bushing members, and said positioner further comprises:

a washer member having a diameter substantially larger than the outer diameter of said bolt member; and a nut for securing one of said anchor bolts to said washer member and said bolt member.

5. A medical image diagnostic apparatus comprising a positioner for securing the medical image diagnostic apparatus to a floor and positioning holes for receiving therethrough anchor bolts implanted upright in said floor, said positioning holes having a diameter substantially larger than that of said anchor bolts, said positioner comprising:

a first cylindrical bushing member having at an eccentric position a through hole of a diameter for rotatably fitting one of said anchor bolts;

a second cylindrical bushing member having at an eccentric position a hole of a diameter for rotatably fitting said first bushing member, said second cylindrical bushing member rotatably fitting in one of said positioning holes;

a bolt member having thereon a thread for engaging with one positioning hole in said medical image diagnostic apparatus and a nut portion for enabling rotation, and having a hole for rotatably fitting therein said second bushing member; and a ring member disposed between said bolt member and said floor for aiding rotation of said bolt member, wherein said bolt member includes a base member below said nut portion, said base member configured to fit within a hole of said ring member.

6. A medical image diagnostic apparatus in accordance with claim 5 wherein said anchor bolts are fabricated from a metallic material.

7. A medical image diagnostic apparatus in accordance with claim 5 wherein said bolt member has a height larger than those of said first and second bushing members, and said positioner further comprises:

a washer member having a diameter substantially larger than the outer diameter of said bolt member; and a nut for securing one of said anchor bolts to said washer member and said bolt member.

* * * * *